United States Patent
Fleischer et al.

(10) Patent No.: US 9,170,226 B2
(45) Date of Patent: Oct. 27, 2015

(54) MICROMECHANICAL SUBSTRATE FOR A DIAPHRAGM WITH A DIFFUSION BARRIER LAYER

(75) Inventors: Maximilian Fleischer, Höhenkirchen (DE); Oliver Freudenberg, München (DE); Harry Hedler, Germering (DE); Markus Schieber, München (DE); Manfred Schreiner, Gauting (DE); Karl Weidner, München (DE); Kerstin Wiesner, Putzbrunn (DE); Jörg Zapf, München (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 113 days.

(21) Appl. No.: 13/877,316

(22) PCT Filed: May 23, 2011

(86) PCT No.: PCT/EP2011/058325
§ 371 (c)(1),
(2), (4) Date: Jun. 26, 2013

(87) PCT Pub. No.: WO2012/041539
PCT Pub. Date: Apr. 5, 2012

(65) Prior Publication Data
US 2013/0264660 A1    Oct. 10, 2013

(30) Foreign Application Priority Data
Sep. 30, 2010  (DE) .......... 10 2010 041 763

(51) Int. Cl.
*H01L 31/058* (2006.01)
*G01N 27/12* (2006.01)
*B81B 3/00* (2006.01)

(52) U.S. Cl.
CPC .............. *G01N 27/12* (2013.01); *B81B 3/0081* (2013.01); *G01N 27/128* (2013.01); *B81B 2201/0214* (2013.01); *B81B 2203/0127* (2013.01)

(58) Field of Classification Search
CPC ................ B81B 3/0081; B81B 2201/0214; B81B 2203/0127; G01N 27/129
USPC ............................ 257/414, 467; 438/48, 49
See application file for complete search history.

(56) References Cited

U.S. PATENT DOCUMENTS

| | | | |
|---|---|---|---|
| 4,647,517 A | 3/1987 | Hersener et al. | |
| 4,784,721 A | 11/1988 | Holmen et al. | |

(Continued)

FOREIGN PATENT DOCUMENTS

| | | |
|---|---|---|
| DE | 34 25 063 A1 | 2/1986 |
| DE | 689 19 870 T2 | 8/1989 |

(Continued)

OTHER PUBLICATIONS
International Search Report for PCT/EP2011/058325; mailed Jan. 18, 2012.

(Continued)

*Primary Examiner* — Matthew E Warren
(74) *Attorney, Agent, or Firm* — Staas & Halsey LLP

(57) ABSTRACT

At least two separate single-crystal silicon layers are formed in a micromechanical substrate which has a diaphragm in a partial region. The diaphragm has a thickness of less than 20 μm and includes part of a first of the single-crystal silicon layers. The substrate construction also includes a heating element configured to generate a temperature of more than 650° C. in at least part of the diaphragm. The substrate includes at least one diffusion barrier layer that reduces the oxidation of the first single-crystal silicon layer.

10 Claims, 2 Drawing Sheets

(56) References Cited

U.S. PATENT DOCUMENTS

| | | | |
|---|---|---|---|
| 5,275,047 | A | 1/1994 | Zabler et al. |
| 5,345,213 | A | 9/1994 | Semancik et al. |
| 5,525,549 | A | 6/1996 | Fukada et al. |
| 5,798,556 | A * | 8/1998 | Hughes et al. ............ 257/414 |
| 6,688,158 | B2 * | 2/2004 | Cunningham et al. ....... 73/24.06 |
| 7,056,751 | B2 | 6/2006 | Faris |
| 7,179,668 | B2 * | 2/2007 | Baney et al. .................... 438/22 |
| 2002/0181110 | A1 | 12/2002 | Bower et al. |
| 2003/0013246 | A1 | 1/2003 | Kubena et al. |

FOREIGN PATENT DOCUMENTS

| | | |
|---|---|---|
| DE | 40 32 559 A1 | 4/1992 |
| EP | 0 953 152 B1 | 5/2002 |
| WO | 00/57151 | 9/2000 |

OTHER PUBLICATIONS

German Office Action for Appln No. 102010041763.7; dated Jan. 13, 2011.

102010041763.7, Sep. 30, 2010, Maximilian Fleischer et al., Siemens Aktiengesellschaft.

\* cited by examiner

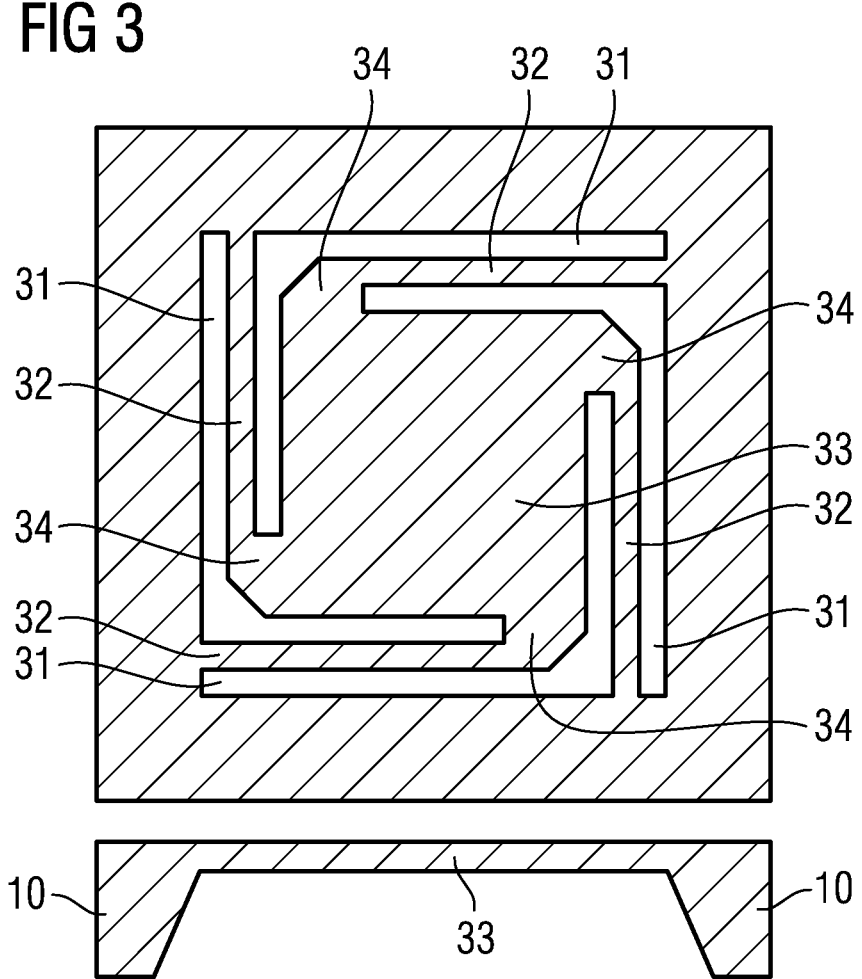

MICROMECHANICAL SUBSTRATE FOR A DIAPHRAGM WITH A DIFFUSION BARRIER LAYER

CROSS REFERENCE TO RELATED APPLICATIONS

This application is the U.S. national stage of International Application No. PCT/EP2011/058325, filed May 23, 2011 and claims the benefit thereof. The International Application claims the benefit of German Application No. 102010041763.7 filed on Sep. 30, 2010, both applications are incorporated by reference herein in their entirety.

BACKGROUND

Described below is a micromechanical substrate including a membrane, and a method for producing the substrate, wherein the membrane is, in particular, a carrier for elements of a sensor.

Gas sensors are increasingly being used in modern technical apparatuses. One example thereof is a leak sensor that detects the occurrence of a single gas. A further example is an exhaust gas sensor that analyzes a mixture of a plurality of gas components. A third example is a gas sensor for fire detection. A further field of use for gas sensors is in respiratory gas analysis, where, by way of example, the presence of alcohols can be detected, or the presence of nitrogen monoxide (NO) for asthma patients.

Gas sensors based on semiconducting metal oxides are of major importance on account of their simple construction and long lifetime. The metal oxide traditionally used is tin dioxide ($SnO_2$), sometimes also $WO_3$. Often, however, other metal oxides and mixtures of different metal oxides and supported catalyst dispersions are also used for improving the sensor properties.

Metal oxide sensors generally have to be heated for operation. The first sensor constructions used for this purpose a small ceramic tube with an inner heating winding as carrier. Modern planar constructions use a usually ceramic substrate, on which an electrical heating structure, for example a platinum heating meander, is fitted on the rear side, and an electrode structure for measuring the resistance of the semiconducting sensor layer is fitted on the front side. The ceramic substrate is then suspended in a housing by small wires (usually composed of platinum).

However, this construction technology is cost-intensive and complex, since in part it involves manual work. In order to reduce the cost and complexity, micromechanical constructions in which the functional elements of the sensor are situated on a membrane having a thickness in the micrometers range, that is to say a very thin membrane, have been developed for the $SnO_2$ sensors. This construction can then be adhesively bonded cost-effectively directly onto a housing or a PCB since the membrane has a high thermal insulation relative to the surroundings and the silicon carrier is therefore practically at room temperature despite the heated membrane. Contact-making is implemented cost-effectively by Al or Au wire bonding.

The membrane used can be realized for example as a silicon nitride membrane. For production purposes, to put it in simplified terms, a silicon wafer is coated with the silicon nitride and a part of the silicon wafer is then removed by a volume etch. EP 0 953 152 B1 discloses the production of a membrane substrate using a silicon-on-insulator wafer (SOI).

The metal oxide $SnO_2$ can be used well on the known membranes, but has a whole series of disadvantages such as, for example:

high variation in manufacturing tolerance of the sensitive properties,
long run-up behavior after every switch-on,
lack of stability in the exhaust gas.

Significant improvements in all these properties are exhibited by more recent metal oxides such as gallium oxide ($Ga_2O_3$), for example described in M. Fleischer, "Advances in Application Potential of Solid State Gas Sensors: High-Temperature Semiconducting Oxides and Ambient Temperature GasFET Devices", Measurement Science and Technology 19 (2008), 1-18. However, this material has to be operated at temperatures of 650-900° C. The known micromechanical constructions having a membrane are not suitable for this purpose on account of a lack of thermal stability, since the continuous conversion of tension into compressive stresses leads to fracture of the membrane. By way of example, in EP 0 953 152 B1, the substrate is heated using a CMOS-compatible heater structure that is likewise not suitable for such temperatures.

SUMMARY

Described herein are a substrate construction which is thermally stable to significantly beyond 650° C. and a method for producing such a substrate construction.

The substrate construction includes a substrate, which has at least two separate monocrystalline silicon layers. The substrate furthermore has a membrane in a partial region, wherein the thickness of the membrane is less than 200 µm. The membrane includes a part of a first of the monocrystalline silicon layers. Finally, the substrate includes at least one diffusion barrier layer for reducing the oxidation of the first monocrystalline silicon layer. In this case, the diffusion barrier layer covers at least the membrane. In this case, the diffusion barrier layer can lie on the first silicon layer directly, or else indirectly, i.e. in a manner separated by other layers.

Besides the two monocrystalline silicon layers, the substrate includes at least one insulating material such as silicon dioxide ($SiO_2$) or silicon nitride ($Si_3N_4$), which separates the monocrystalline silicon layers. The substrate may be a processed SOI wafer.

The membrane may be thinner than 100 µm and, in a further configuration, thinner than 50 µm. The thinner the membrane, the lower its heat capacity. In the case of a low heat capacity, rapid temperature changes are possible, which is advantageous for operation of, for example, gas sensors on the substrate construction. Furthermore, in the case of a thinner membrane, the insulation capability of the membrane is also increased, which provides for a more uniform temperature of the membrane and thus reduces the internal mechanical stresses thereof as a result of temperature gradients. For a certain mechanical strength, it is in turn advantageous if the membrane is thicker than 2 µm, in particular thicker than 20 µm.

The diffusion barrier layer covers at least the membrane directly or indirectly. The diffusion barrier layer reduces the access of oxygen to the first of the monocrystalline silicon layers. It has been recognized by the inventors that a membrane having a monocrystalline silicon layer can withstand high temperatures better than known silicon nitride membranes, but oxidizes at high temperatures. This oxidation reduces the lifetime of such a construction to values of a few hundred hours with acceptable membrane thicknesses, which is too short. Therefore, advantageously due to the diffusion barrier layer, the access of oxygen to at least a part of the first of the monocrystalline silicon layers is made more difficult and the lifetime is thus significantly increased. As a result, a membrane substrate is provided which is able to withstand temperatures of more than 650° C. This in turn makes it possible to use gas sensor materials that only function at such high temperatures on membrane substrates.

The diffusion barrier layer may be formed of one or more of the materials platinum, platinum silicide, silicon nitride and silicon carbide. As is known, these materials have high thermal stability and low permeability to oxygen. SiO2, by contrast, is not suitable as a diffusion barrier layer. A multi-layered construction using a plurality of materials is also appropriate as diffusion barrier layer. It is particularly advantageous if the first monocrystalline silicon layer is covered by the diffusion barrier layer both on the top side and on the underside, since oxygen is then prevented from penetrating via the two large boundary surfaces of the silicon layer.

The second of the monocrystalline silicon layers may form a carrier frame for the substrate construction. This advantageously ensures that the membrane is produced more easily, since silicon can be processed in a simple manner using known etching techniques.

In one configuration, the membrane is connected to the rest of the substrate via webs. In other words, there is no complete connection of the edge of the membrane to the surrounding substrate, rather cutouts are present, which decouple a part of the edge of the membrane from the rest of the substrate and thus make the membrane freely suspended in parts. This increases the resistance of the membrane toward thermomechanical loads, since the membrane has greater freedom to stretch, for example, without having to deform significantly in the process.

It is particularly advantageous if the webs have an angled portion, or in other words if the webs change their running direction in the horizontal. It is particularly advantageous if the webs have a long element running parallel to the membrane side edge and there is an angled portion at the end of the long element, by which angled portion the web is connected to the membrane. What is achieved by the long elements is that a mechanical loading as a result of expansion of the membrane at a high operating temperature can be reduced particularly well by a slight rotation of the membrane.

Expediently, the substrate construction includes a heating element, which is designed to generate a temperature of more than 650° C. in at least one part of the membrane. The heating element can be realized as an electrical resistance heater, for example. Such heaters are realized for example using layers of greater or lesser thickness that are composed of structured platinum. An electrical heating system realized as a transistor can also be used. In an alternative configuration, it is also possible for the heater to be provided away from the membrane, for example as a radiation source directed at the membrane.

Using the substrate construction, a gas sensor can advantageously be constructed by adding to the substrate construction a gas-sensitive element applied at least partly on the membrane. By way of example, a metal oxide can be applied to the membrane and the resistance of the metal oxide can be evaluated as gas measurement signal.

The method described herein for producing a substrate construction involves providing a substrate, wherein the substrate has at least two separate monocrystalline silicon layers. By way of example, an SiO wafer can be used for this purpose. A membrane is produced in a partial region of the substrate, the thickness of the membrane being less than 200 µm, in particular less than 50 µm, wherein the membrane forms a part of a first of the monocrystalline silicon layers. Finally, at least one diffusion barrier layer for reducing the oxidation of the first monocrystalline silicon layer is produced, wherein the diffusion barrier layer covers at least the membrane. Preferably, in each case at least one diffusion barrier layer is produced on the top side and underside of the first monocrystalline silicon layer.

BRIEF DESCRIPTION OF THE DRAWINGS

These and other aspects and advantages will become more apparent and more readily appreciated from the following description of the exemplary embodiments, taken in conjunction with the accompanying drawings in which the features are illustrated schematically and of which:

FIG. 3 is a plan view and a section through a structuring of a membrane substrate.

DETAILED DESCRIPTION OF THE PREFERRED EMBODIMENT

Figure 1:
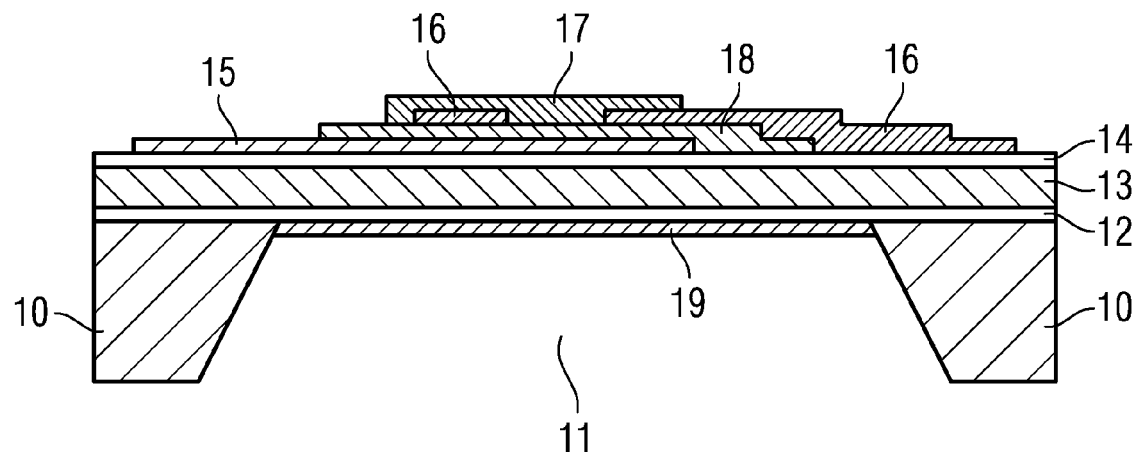
FIG. 1 is a cross sectional side view of a gas sensor construction with heating element and gas sensor arranged one above the other.

Reference will now be made in detail to the preferred embodiments, examples of which are illustrated in the accompanying drawings, wherein like reference numerals refer to like elements throughout.

FIG. 1 shows a first exemplary embodiment of a gas sensor based on gallium oxide, this gas sensor being realized on a membrane substrate. In this case, FIG. 1 illustrates a section through the gas sensor and the membrane substrate. In this case, the illustration is not true to scale; most of the thicknesses of layers are illustrated in a highly exaggerated manner relative to the lateral extents. In this case, the section is furthermore not illustrated completely, since the membrane is not continuously connected to the rest of the substrate, and incisions should therefore be visible in the sectional diagram. These have been omitted, however, for the sake of better clarity.

The membrane substrate is carried by a frame 10 composed of monocrystalline silicon. Only two beveled pieces of the frame 10 can be discerned in the sectional diagram in FIG. 1, but the pieces form a continuous frame 10 around the membrane in the first exemplary embodiment. The membrane itself is formed by a layer sequence of an insulation layer 12 composed of silicon dioxide, a membrane layer 13 composed of monocrystalline silicon and an upper diffusion barrier layer 14, which is platinum silicide in this example. Below the membrane, a lower diffusion barrier layer 19 is provided in the interior of the frame 10, the lower diffusion barrier layer likewise formed of platinum silicide in the first exemplary embodiment. The layer sequence forms the membrane in the region in which the frame 10 has a cutout 11. In this example, the thickness of the membrane is 30 µm. The diffusion barrier layer 14 simultaneously serves as a layer for electrical insulation. If the diffusion barrier layer 14 itself does not have a sufficiently insulating effect, it is possible, for example, to produce a further layer on or below the diffusion barrier layer 14. The further layer may substantially be formed of SiO2 and/or Al2O3. SiO2 is particularly well suited to this owing to good adhesion to the support, simple production by thermal oxidation, furthermore owing to good stability at high temperatures and also owing to only little further oxidation during further high-temperature processes.

Various elements are then accommodated on the membrane and together form a gas sensor construction. For this purpose, from one side of the membrane substrate proceeding from a region above the frame 10, a heater layer 15 leads onto the membrane. In the region of the membrane, the heater layer 15 is structured such that a heating meander is formed. The electrical resistance is significantly increased in the region of the heating meander and electrical heating of the membrane is thus possible. The heater layer 15 is furthermore covered by an insulation layer 18 composed of silicon nitride in the region of the membrane.

The electrical heater can also be used as a temperature sensor by the temperature response of the electrical resistance. The heater layer 15 may be formed of platinum as a thin layer having a thickness of, for example, between 0.5 and 2 µm. Alternatively, the heater layer 15 may be formed, for example, of hard alloys of platinum materials, for example Pt/Rh 70/30. In order to avoid destruction of heating by electromigration, in the case of the heater layer 15 corners and angular transitions should as far as possible be avoided and replaced by round structures.

From a further side of the membrane substrate, two gas sensor electrodes 16 lead onto the membrane and onto the insulation layer 18. The gas sensor electrodes 16 form a so-called interdigital electrode structure, also called finger electrode structure, in the region of the membrane on the insulation layer 18. In this case, the finger electrodes typically have spacings of between 5 and 30 µm. A gas sensor layer 17 composed of polycrystalline gallium oxide is applied on the finger electrode structure. Such a layer is usually produced by a sputtering method using a shadow mask. The layer thickness of the $Ga_2O_3$ layer is preferably between 0.5 and 3 µm. In alternative embodiments of the gas sensor, instead of the gallium oxide it is also possible to use a series of other metal oxides, for example $CeO_2$, $TiO_2$, $WO_3/TiO_2$ mixed oxides, NiO, chromium titanium oxides ($Cr_{2-x}Ti_xO_3$, $x \leq 0.5$) and materials from the group of the perovskites ($SrTiO_3$, $BaTiO_3$, temperature-independent cuprates such as $LaCu_{1-x}Fe_xO_{3-y}$.

The substrate shown forms a high-temperature-resistant membrane construction through the use of monocrystalline silicon as essential membrane material and also through the use of silicon as material for the frame 10. This material can be processed well using the methods of microtechnology. The silicon as membrane material ensures, besides sufficient mechanical stability, primarily the required temperature resistance. Since the material is already in the monocrystalline state, no further build-up of mechanical stresses that would lead to the impediment of the membrane function can take place at high temperatures.

If the insulation layer between heating system and structure of the $Ga_2O_3$ sensor does not have a sufficient insulation capability, it may be replaced vertically by a three-layer system of insulator, planar Pt electrode, insulator with the central electrode grounded. It is thereby possible to shield creepage currents from the heating system to the $Ga_2O_3$ sensor, which currents can bring about a corruption in the measurement of the resistance of the $Ga_2O_3$.

Figure 2:
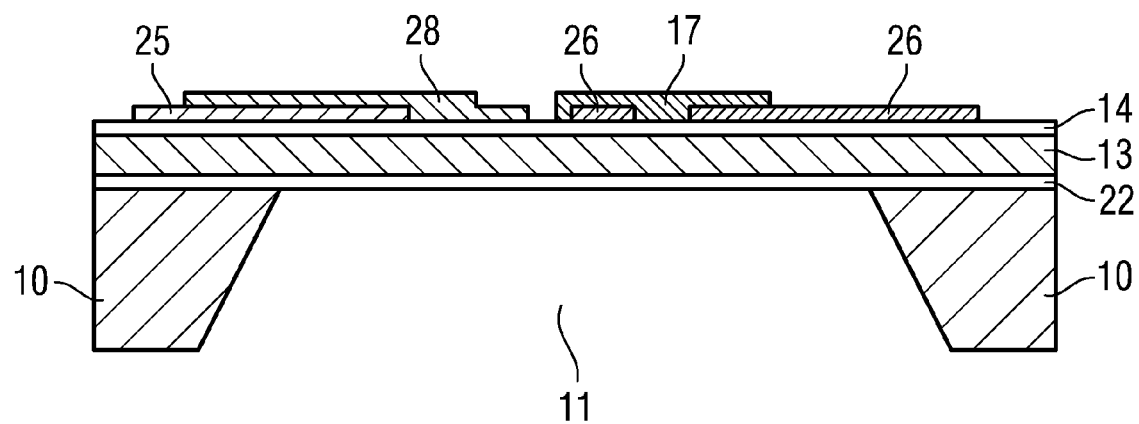
FIG. 2 is a cross sectional side view of a gas sensor construction with heating element and gas sensor arranged alongside one another.

A second exemplary embodiment of a membrane substrate is illustrated in FIG. 2. In this case, the same limitations as for FIG. 1 are applicable with regard to the illustration, and so the illustration is not true to scale, inter alia.

As in the case of the membrane substrate in accordance with the first exemplary embodiment, the substrate is carried by a frame 10 composed of a crystalline silicon. By comparison with the first exemplary embodiment, however, the layer sequence that forms the membrane is altered. Thus, in the second exemplary embodiment, the membrane is formed by an insulation and diffusion barrier layer 22 composed of silicon nitride, the membrane layer 13 composed of monocrystalline silicon and the upper diffusion barrier layer 14. Since, in the second exemplary embodiment, the insulator layer between the monocrystalline layers of the frame 10 and the membrane layer 13 is already formed by silicon nitride, an additional diffusion barrier layer below the membrane is unnecessary. In the first exemplary embodiment, by contrast, the insulator layer is formed by a silicon dioxide layer, which is not suitable as a diffusion barrier layer.

A gas sensor construction is realized on the membrane in the second exemplary embodiment as well. In this case, however, in order to simplify production, the various elements are realized alongside one another instead of one on top of another. Thus, in this case, a shortened platinum heater 25 leads into the region of the membrane to a significantly lesser extent. The shortened platinum heater 25 occupies only approximately half of the membrane area. The shortened platinum heater 25 is in turn covered by an insulation layer 28. Alongside the shortened platinum heater 25, second gas sensor electrodes 26 once again lead into the region of the membrane, where they are once again covered by a gas sensor layer 17. In the second exemplary embodiment, the good thermal conductivity of the silicon membrane serves for distributing the heat on the membrane and thus indirectly for the heating of the gas sensor. This constitutes a construction which is significantly simplified with regard to the required processes.

FIG. 3 shows a plan view and a section through a structuring of the membrane substrate. The frame 10 is once again shown in this case, the frame running around the entire membrane substrate. The membrane 33 is situated in the frame 10. In the plan view it is evident that the membrane 33 is not continuously connected to the frame 10. Rather, the membrane 33 is suspended on webs 32. The webs 32, of which there are up to four, in this case begin on the inner side of the frame 10, and run parallel to the inner edge of the frame 10 until they respectively reach an angled portion 34 and join there with the actual membrane area 33. In order to achieve this structuring, the substrate has corresponding cutouts 31.

Since very high temperature differences between the temperature of the frame 10 and operating temperature occur, particular account has to be taken of the linear expansion of the membrane and the thermomechanical stress that arises. This is done by the cutouts 31. The cutouts ensure a resilient suspension of the membrane 33. The webs 32 take up mechanical stresses from the membrane 33 and distribute them over long spring excursions. Furthermore, the webs 32 act, of course, as a platform for the electrical leads to the membrane 33.

The construction shown allows the high mechanical loads that occur at high operating temperatures to have as little destructive effect on the membrane 33 as possible. In this case, the mechanical loads result firstly from the high difference in the temperatures between the frame 10 and the membrane 33 and secondly from different coefficients of thermal expansion between the different materials from which the membrane 33 and the overlying layers are constructed. In this case, the different coefficients of expansion lead to a warping of the membrane 33. In this case, the resilient suspension by the webs 32 allows a relatively substantial deformation for the membrane 33. The total expansion which the membrane 33 experiences as a result of the high operating temperature can likewise be cushioned very well by the webs 32 by virtue of the membrane rotating for example slightly in its suspension via the webs 32. In this case, the critical values for the mechanical loads are not exceeded even at very high operating temperatures of 800° C. or more.

At the high temperatures during operation, particular attention should also be paid to the adhesion between individual layers of the construction. Generally, it is necessary to apply conductive metal layers composed of platinum, for example, on an insulating support composed of silicon dioxide, for example, with good adhesive strength even at high temperatures. Since the adhesion of platinum on SiO2 is insufficient, adhesion-promoting layers are required for this purpose. The traditional metallic adhesion promoters such as Ti, Cr, W, Ta as thin metallic layers cannot be used here, since they alloy with the Pt at the high temperatures, nor are they sufficiently stable with respect to oxidation. Oxidic adhesion promoters, for example layers composed of stoichiometric oxides, are advantageously used for this purpose. These layers may have a thickness of between 50 nm and 200 nm. Advantageously, the oxidic adhesion promoters can neither oxidize subsequently nor alloy with the platinum. By way of example, Ga2O3, for example as a sputtered layer, but also other thermally stable oxides, such as Al2O3, CeO2, TiO2 or Zr2O3, are very well suited here. However, some of the oxides have the disadvantage that they can migrate into the Ga2O3 of the gas sensor layer 17 and electrically dope the Ga2O3.

It is readily apparent that the embodiments described present a substrate which allows a practical and small construction of high-performance gas sensors having a chip size of 1-2 mm2. The heating power is reduced by approximately one order of magnitude compared with conventional substrates by virtue of the strong thermal insulation of the membrane.

Furthermore, the extremely small thermal mass allows temperature-transient operation of the sensors, which, in association with a corresponding signal evaluation, allows the stabilization of the sensor base line and also the improvement of gas detection (selectivity or identification of multi-gas mixtures). The non-critical bending deformation leads to an increased lifetime compared with known solutions with supercritical shear stress.

One possible process sequence for producing such a substrate may be manifested as follows:
1. The starting material is an SOI wafer, wherein the so-called "device layer" corresponds to the membrane layer 13 and thus substantially makes up the thickness of the membrane.
2. Deposition of silicon nitride as a mask for a volume etch on the wafer rear side, e.g. by a CVD process and patterning.
3. Deposition of silicon oxide as an insulator layer on the wafer front side, e.g. by a CVD process and patterning.
4. Sputtering of Pt for the heater layer 15, patterning by photolithography and ion beam etching.
5. Deposition of silicon oxide as an insulation layer 18, 28, e.g. by a CVD process and subsequent patterning.
6. Dry etching of the silicon device layer; the SiO2 serves as masking in this case.
7. KOH volume etching of the wafer from the rear side in order to produce the membrane; the Si3N4 serves as masking in this case.
8. Dry etching of the SiO2 from the wafer rear side.
9. Sputtering of Ga2O3 for the gas sensor layer 17 through a shadow mask.
10. Application of a porous catalyst filter by a jetting/dispensing process.

An improvement in the gas sensitivity can be achieved by the noble-metal-containing leads such as the heater layer 15, 25 and the gas sensor electrodes 16, 26 being covered by passivation layers, for example by glass paste or by SiO2 deposited by CVD. This prevents the undesired conversion of the gases to be detected at the reactive, catalytically active leads. The covering of the leads is also advantageous for use in corrosive industrial environments and exhaust gases.

In order to improve the gas selectivity, additional porous thick layers can also be applied to the gas sensor layer 17. The layers can act firstly as filters for reducing cross-sensitivities by virtue of the fact that undesirable, disturbing gases are already converted during diffusion through the hot porous thick layer, the gases no longer reach the gas sensor layer 17 and they can no longer disturb the measurement of the actual target gas. Oxidic materials such as Ga2O3, Al2O3 are suitable as material for the thick layers. Secondly, porous thick layers can also have an activating effect on the target gas to be detected. During diffusion through the hot porous thick layer, molecules that are otherwise slow to react are activated and their measurement effect at the gas sensor layer 17 is increased. For activation purposes it is necessary to use a thick-layer material having activating properties (e.g. Ga2O3).

Temperature-transient operation of the sensors with multivariate signal evaluation for improving the selectivity and identifying complex odor patterns is possible with the arrangement described herein, since the small thermal mass allows a rapid temperature change.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in Superguide v. DIRECTV, 358 F3d 870, 69 USPQ2d 1865 (Fed. Cir. 2004).

The invention claimed is:

1. A substrate construction, comprising:
a substrate having at least two separate monocrystalline silicon layers and a membrane in a partial region, the membrane having a thickness of less than 200 μm and forming a part of a first monocrystalline silicon layer; and
at least one diffusion barrier layer formed of at least one material selected from the group consisting of platinum, platinum silicide, silicon nitride and silicon carbide, covering at least the membrane, formed at least on a top side of the first monocrystalline silicon layer, and reducing oxidation of the first monocrystalline silicon layer.

2. The substrate construction as claimed in claim 1, wherein the at least one diffusion barrier layer is formed on both the top side and an underside of the first monocrystalline silicon layer.

3. The substrate construction as claimed in claim 1, wherein the membrane is connected to the rest of the substrate via webs.

4. The substrate construction as claimed in claim 3, wherein the webs each have at least one angled portion.

5. The substrate construction as claimed in claim 4, further comprising a heating element generating a temperature of more than 650° C. in at least one part of the membrane.

6. The substrate construction as claimed in claim 5, further comprising: an underlying insulating layer; and an adhesion-promoting layer substantially consisting of a metal oxide provided between the underlying insulating layer and at least one of the heating element and another metallic layer.

7. The substrate construction as claimed in claim 6, further comprising a gas-sensitive element applied at least partly on the membrane.

8. A method for producing a substrate construction, comprising:
   providing a substrate having at least two separate monocrystalline silicon layers; producing a membrane in a partial region of the substrate, the membrane having a thickness of less than 200 µm and forming a part of a first monocrystalline silicon layer; and producing a diffusion barrier layer formed of at least one material selected from the group consisting of platinum, platinum silicide, silicon nitride and silicon carbide, covering at least the membrane, formed at least on a top side of the first monocrystalline silicon layer, and reducing oxidation of the first monocrystalline silicon layer.

9. The method as claimed in claim 8, wherein a silicon-on-insulator wafer is used in producing the substrate.

10. The method as claimed in claim 9, wherein said producing of the at least one diffusion barrier layer forms the at least one diffusion barrier layer on both the top side and an underside of the first monocrystalline silicon layer.

* * * * *